US00PP27274P3

(12) United States Plant Patent
Bradford et al.

(10) Patent No.: US PP27,274 P3
(45) Date of Patent: Oct. 18, 2016

(54) CHERRY TREE NAMED 'ARVIN BRUCE'

(50) Latin Name: *Prunus avium*
Varietal Denomination: Arvin Bruce

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 101 days.

(21) Appl. No.: 14/544,249

(22) Filed: Dec. 15, 2014

(65) Prior Publication Data

US 2016/0174435 P1 Jun. 16, 2016

(51) Int. Cl.
*A01H 5/08* (2006.01)

(52) U.S. Cl.
USPC ..... Plt./181

(58) Field of Classification Search
USPC ..... Plt./181
See application file for complete search history.

(56) References Cited

U.S. PATENT DOCUMENTS

PP12,859 P2 8/2002 Bradford
PP15,512 P3 * 2/2005 Bradford ..... Plt./181

* cited by examiner

*Primary Examiner* — June Hwu

(57) ABSTRACT

The present invention relates to a cherry tree, *Prunus avium*, and more particularly to a new and distinct variety broadly characterized by a medium size, moderately vigorous, hardy, self-unfruitful, productive and regular bearing tree. The fruit matures under the ecological conditions described in early May, with first picking on May 3, 2014. The fruit is uniformly medium to large in size, very good in flavor, somewhat oblate in shape, freestone in type, moderately firm in texture, heat tolerant, red to yellowish pink in flesh color, deep red in skin color, and it has a medium length stem that is strongly attached to the fruit.

1 Drawing Sheet

Botanical classification: *Prunus avium.*
Varietal denomination: 'ARVIN BRUCE'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'Arvin Bruce'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2002 one such house containing 'Glenred' (U.S. Plant Pat. No. 12,859) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified and germinated as a group with the label 'Glenred House'. They were grown as seedlings on their own root in our greenhouse, and upon reaching dormancy transplanted to a cultivated area of our experimental orchard located near Le Grand, Calif. in Merced County (San Joaquin Valley). During the summer of 2008 the claimed variety was selected by us as a single tree from the group of seedlings described above. Subsequent to origination of the present variety of cherry tree, we asexually reproduced it by budding and grafting in the experimental orchard described above, and such reproductions were true to the original tree in all respects. The reproduction of the variety included the use of 'Colt' (unpatented) rootstock, upon which the present variety was compatible and true to type.

The present variety is most similar to its seed parent, 'Glenred' (U.S. Plant Pat. No. 12,859) cherry, by being self-unfruitful, by blooming during the early season, by having reniform glands, by being productive, and by producing fruit that is full red in skin color, somewhat oblate in shape, moderately firm, sweet, and fairly crack resistant, but is distinguished therefrom by producing cherries that are somewhat larger in size, that are a lighter red in flesh color, that are fully freestone instead of semi-freestone, that ripen about five days earlier, and that have stems that are more strongly attached.

The present variety is also similar to 'Glenrock' (U.S. Plant Pat. No. 15,512) cherry by being self-unfruitful, by blooming during the early season, by having reniform glands, by being productive, and by producing fruit that is full red in skin color, that is partially red in flesh color, that is oblate in shape, that is somewhat freestone in type, that is sweet in flavor, and that has a medium length stem with strong attachment, but is distinguished therefrom by producing cherries that are somewhat larger in size, that are not quite as firm, and that ripen about 10 days earlier.

SUMMARY OF VARIETY

In summary, the present cherry variety is characterized by a medium size, moderately vigorous, hardy, self-unfruitful, productive and regular bearing tree. The fruit matures under the ecological conditions described in early May, with first picking on May 3, 2014. The fruit is uniformly medium to large in size, very good in flavor, somewhat oblate in shape, freestone in type, moderately firm in texture, heat tolerant, red to yellowish pink in flesh color, deep red in skin color, and it has a medium length stem that is strongly attached to the fruit.

DRAWING

The accompanying photograph displays three fruits with the stems attached, four whole fruits detached from the stems to exhibit the skin color and form, two half fruits sectioned to reveal the flesh and fibers, an individual stone, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 6, 2014, on the original tree during its twelfth growing season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: 'Glenred' cherry (U.S. Plant Pat. No. 12,859).
Pollen parent: Unknown.

TREE

Size: Medium, maintained to a height of 11' [3.35 m.] and a spread of 6' [1.83 m.] after twelve growing seasons utilizing typical pruning.

Vigor: Medium vigor, responding typically to irrigation and fertilization. The tree should be grown on a standard commercial rootstock for production purposes.

Growth: Upright and medium dense.

Form: Central leader.

Hardiness: Hardy with respect to central California winters.

Heat tolerance: Observed to perform adequately in both central California and southern San Joaquin Valley climatic conditions, which typically include extended periods of heat.

Drought tolerance: Variety is developed for commercial orchards and requires regular irrigation.

Production: Productive.

Fertility: Self-sterile, must be cross pollinated by another early seasonal blooming cherry variety, such as 'Sweet Fruitful' (U.S. Plant Pat. No. 21,926).

Bearing: Regular bearer, with no crop failures observed.

Trunk:

*Size.*—Medium, reaching a maximum diameter of 3¾" [95.3 mm.] after the twelfth growing season.

*Texture.*—Medium smooth.

*Bark color.*—A Dark grayish reddish brown [47. d.gy.rBr] and Light brownish gray [63. l.brGy] variegation.

*Lenticels.*—Approximate Number Per Square Inch: 8. Color: Deep yellowish brown [75. deep yBr]. Average Size: Length is 7/16" [11.1 mm.] with a width of ⅛" [3.2 mm.]. Shape: Eye-shaped, elongated.

Branches:

*Size.*—Diameter of main scaffold measured 12" above the first hanger is 2½" [63.5 mm.].

*Texture.*—Smooth on first and second year wood, increasing roughness with age.

*Color.*—1st Year Wood topside: Grayish red [19. gy.R]. 1st Year Wood underside: Brilliant yellow green [116. brill.YG]. 2nd Year Wood: Strong brown [55. s.Br]. 3rd Year and Older Wood: Grayish reddish brown [46. gy.rBr].

*Lenticels.*—Number Per Square Inch: About 14 on second year wood. Color: Moderate yellowish brown [77. m.yBr]. Average Size: ⅛" [3.2 mm.] in length and 1/32" [0.8 mm.] in width on second year wood. Shape: Elongated.

Leaves:

*Size.*—Large. Average Length: 5¾" [146.1 mm.]. Average Width: 2⅝" [66.7 mm.].

*Arrangement.*—Alternate.

*Thickness.*—Medium.

*Form.*—Elliptical.

*Apex.*—Acuminate.

*Base.*—Rounded.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 1½" [38.1 mm.]. Average Thickness: 3/32" [2.4 mm.]. Color: Dark grayish red [20. d.gy.R] on the topside, Brilliant yellow green [116. brill.YG] on the underside.

*Stipules.*—Number: 2 per leaf at development stage. Average Length: ½" [12.7 mm.]. Color: Grayish purplish red [262. gy.pR] toward the base, Light yellow green [119. l.YG] toward the apex. Surface: Smooth.

*Glands.*—Number: 2 to 4 per leaf. Position: Usually occurring in alternate pairs on the petiole near the base of leaf blade. Size: Large, about 3/64" [1.2 mm.] in length. Form: Reniform. Color: Deep red [13. deep R] toward the center, Light orange [52. l.O] around the sides.

*Leaf buds.*—Pointed, medium.

Flower buds:

*Hardiness.*—Hardy, with respect to central California winters.

*Diameter.*—Typically 5/16" [7.9 mm.] 3 days before bloom.

*Length.*—Typically ⅝" [15.9 mm.] 3 days before bloom.

*Form.*—Free, not touching.

*Surface.*—Non-pubescent.

*Tip color.*—White [263. White].

Flowers: Perfect, complete, perigynous, usually a single pistil, typically about twenty stamens, five sepals and petal locations alternately positioned.

*Average flower diameter.*—1 7/16" [36.5 mm.].

*Average flower depth.*—½" [12.7 mm.] when fully open.

*Number of petals.*—Usually five, extra petals or fragments rarely observed.

*Petal arrangement.*—Overlapping.

*Petal shape.*—Circular to slightly oval.

*Petal margin.*—Somewhat wavy with occasional serrations.

*Average petal diameter.*—⅝" [15.9 mm.].

*Average petal length.*—⅝" [15.9 mm.].

*Petal apex.*—Rounded with a small notch on some.

*Petal base.*—Rounded to somewhat cuneate.

*Petal color.*—White [263. White] on both sides.

*Anther color.*—Pale yellow [89. p.Y].

*Pollen.*—Anthers produce a moderate amount of Brilliant yellow [83. brill.Y] pollen.

*Stigma color.*—Light greenish yellow [101. l.gY].

*Stigma position.*—Typically located about even with the nearby anthers.

*Ovary.*—Non-pubescent.

*Sepal color.*—Deep reddish orange [36. deep rO] over Vivid greenish yellow [97. v.gY] on the outer surface. The inner surface is Pale yellow green [121. p.YG].

*Sepal outer surface.*—Pubescent.

*Sepal length.*—¼" [6.4 mm.].

*Sepal width.*—3/16" [4.8 mm.].

*Sepal apex.*—Rounded to elliptical to match the sepal length and width.

*Sepal margin.*—Fairly smooth.

*Average pistil length.*—⅝" [15.9 mm.].

*Average stamen length.*—9/16" [14.3 mm.].

*Fragrance.*—Moderate.

*Bloom density.*—Heavy.

*Blooming period.*—Early, blooms at the same time as 'Glenred' (U.S. Plant Pat. No. 12,859).

*Onset of bloom.*—One percent on Mar. 8, 2014.

*Date of full bloom.*—Mar. 19, 2014.

*Duration of bloom.*—One to two weeks, dependent on ambient temperature.

*Number per cluster.*—Usually 2 to 8, 5 average.

FRUIT

Maturity when described: Firm ripe, May 6, 2014.

Date of first picking: May 3, 2014.

Date of last picking: May 11, 2014.

Size: Uniform, medium to large.

*Average diameter axially.*—1" [25.4 mm.].

*Average diameter across suture plane.*—1 1/16" [27.0 mm.].

*Average diameter across cheek plane.*—1 5/16" [33.3 mm.].

*Typical weight.*—0.48 ounces [13.6 grams].

Form: Uniform, somewhat oblate, most are compressed axially and around the suture.

*Axial view form.*—Elliptical.

*Suture plane form.*—Oval to round.

*Cheek plane form.*—Oblate.

Suture: An inconspicuous line located in a shallow trough, extending from the base to the pistil point.

Ventral surface: Rounded, lipped slightly throughout.

Lips: Mostly equal.

Cavity: Flaring, circular, suture showing on one side.

*Depth.*—⅛" [3.2 mm.].

*Breadth.*—½" [12.7 mm.].

Base: Rounded if viewed in the suture plane, slightly cordate if viewed parallel to the suture.

Apex: Rounded if viewed in the suture plane, somewhat cordate if viewed parallel to the suture.

Pistil point: A Light yellowish brown [76. l.yBr] inconspicuous dot.

Stem: Medium.

*Average length.*—1 9/16" [39.7 mm.].

*Average diameter.*—1/16" [1.6 mm.].

Stem attachment: Strong.

Skin:

*Thickness.*—Medium.

*Surface.*—Smooth.

*Tenacity.*—Tenacious to the flesh.

*Astringency.*—Moderate.

*Tendency to crack.*—None observed in dry seasons, fairly resistant to cracking in wet season.

*Color.*—Very deep red [14. v.deep R] over a Vivid red [11. v.R] background.

Flesh:

*Color.*—Light yellowish pink [28. l.yPk] with Moderate red [15. m.R] streaking and flecking throughout, Pale orange yellow [73. p.OY] fibers visible.

*Surface of pit cavity.*—Covered with Pale yellowish pink [31. p.yPk] fibers.

*Amygdalin.*—Moderate.

*Juice.*—Abundant, somewhat watery.

*Juice color.*—Vivid red [11. v.R].

*Texture.*—Moderately firm, melting.

*Fibers.*—Abundant, thick.

*Ripens.*—Fairly even, slightly earlier at the apex.

*Heat tolerance.*—Observed to remain firm during extended periods of heat prior to and during the harvest season.

*Flavor.*—A balance of acid and sugar, typically 18 to 20 brix.

*Aroma.*—Slight.

*Eating quality.*—Very good.

STONE

Type: Freestone.

Form: Oval.

Hilum: Narrow, oval.

Base: Rounded.

Apex: Rounded.

Sides: Equal.

Surface: Fairly smooth.

External color of stone: Light orange yellow [70. l.OY] when first removed.

Pit wall color when cracked: Pale yellow [89. p.Y].

Cavity surface color: Pale orange yellow [73. p.OY].

Average pit wall thickness: 1/16" [1.6 mm.].

Average width: ⅜" [9.5 mm.].

Average length: ⅜" [9.5 mm.].

Average breadth: 5/16" [7.9 mm.].

Tendency to split: None observed.

Kernel:

*Form.*—Oval.

*Skin color.*—Yellowish white [92. yWhite] when first removed.

*Pellicle color.*—Grayish yellow [90. gy.Y].

*Vein color.*—Grayish yellow [90. gy.Y].

*Taste.*—Bitter.

*Viable.*—Yes.

*Average width.*—¼" [6.4 mm.].

*Average length.*—¼" [6.4 mm.].

*Amygdalin.*—Abundant.

USE

Market: Fresh market and long distance shipping.

Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is most similar to its seed parent, 'Glenred' (U.S. Plant Pat. No. 12,859) cherry, by being self-unfruitful, by blooming during the early season, by having reniform glands, by being productive, and by producing fruit that is full red in skin color, somewhat oblate in shape, moderately firm, sweet, and fairly crack resistant, but is distinguished therefrom by producing cherries that are somewhat larger in size, that are a lighter red in flesh color, that are fully freestone instead of semi-freestone, that ripen about five days earlier, and that have stems that are more strongly attached.

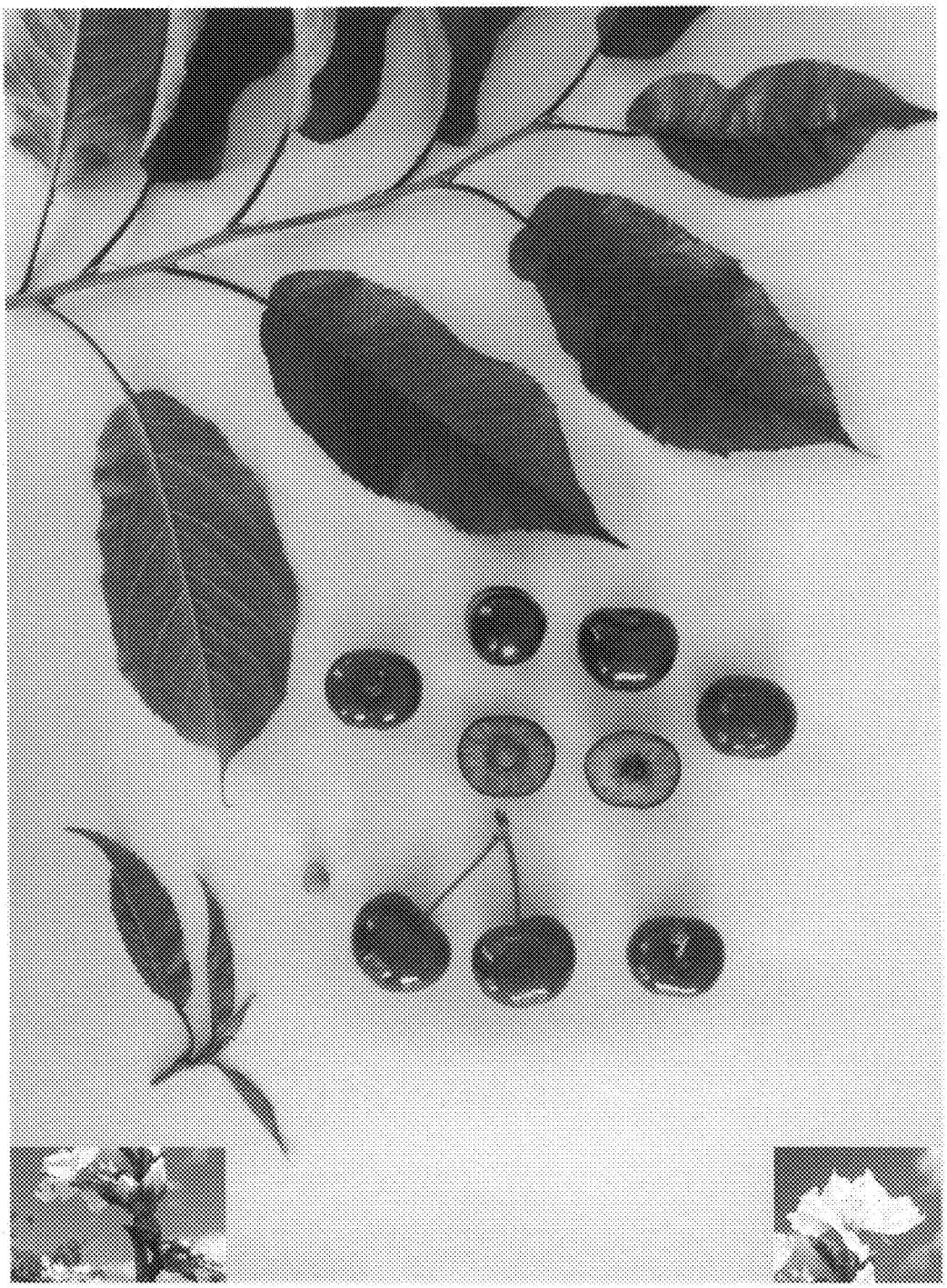

* * * * *